US006849640B2

(12) United States Patent
Ennis et al.

(10) Patent No.: US 6,849,640 B2
(45) Date of Patent: Feb. 1, 2005

(54) THERAPEUTIC 1H-PYRIDO [4,3-B] INDOLES

(75) Inventors: Michael D. Ennis, Portage, MI (US); Kristine E. Frank, Portage, MI (US); Robert L. Hoffman, Kalamazoo, MI (US); Jian-Min Fu, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 10/214,405

(22) Filed: Aug. 6, 2002

(65) Prior Publication Data

US 2003/0060464 A1 Mar. 27, 2003

Related U.S. Application Data

(60) Provisional application No. 60/310,890, filed on Aug. 8, 2001.

(51) Int. Cl.[7] .................... A61K 31/437; A61K 31/435; C07D 471/04; A61P 25/22
(52) U.S. Cl. .................... 514/292; 514/291; 514/228.2; 514/232.8; 546/86; 546/85; 544/60; 544/128
(58) Field of Search ...................... 546/86, 85; 544/60, 544/128; 514/292, 291, 228.2, 232.8

(56) References Cited

U.S. PATENT DOCUMENTS

| 3,657,254 | A | | 4/1972 | Barkov et al. |
| 4,337,250 | A | | 6/1982 | Welch et al. |
| 4,478,750 | A | | 10/1984 | Gadient |
| 4,938,949 | A | | 7/1990 | Borch et al. |
| 5,252,580 | A | * | 10/1993 | Takahashi et al. .......... 514/292 |
| 5,563,147 | A | * | 10/1996 | Gilmore et al. ............. 514/292 |
| 6,057,325 | A | | 5/2000 | Kennis et al. |

FOREIGN PATENT DOCUMENTS

| EP | 0 353 983 | 2/1990 |
| EP | 0 385 722 | 9/1990 |
| EP | 0 705 832 | 4/1996 |
| GB | 2 120 662 | 12/1983 |
| JP | 63-163347 | 7/1988 |
| WO | WO 94/14771 | 7/1994 |
| WO | WO 00/00487 | 1/2000 |
| WO | WO 02/24700 | 3/2002 |

OTHER PUBLICATIONS

Vanhoenacker P et al. (2000) TIPS 21:70–77.*
Wijngaarden I et al. (1993) Recl. Trav. Chim. Pays–Bas 112:126–230.*
Pandey et al. Journal of Psychiatry & Neuroscience, 1995, 20(3): 215–25.*
Dourish CT. Obesity Research, 1995, 3 Suppl 4 : 449S–462S.*
Bourin et al. Current Opinion in Investigational Drugs, 2001, 2(2): 259–65.*
"Synthesis of 2,3,4,4a,5,9b–Hexahydro–1$H$–pyrido [4,3–$b$] indole Derivatives and Their Central Nervous System Activities", by Yasutaka Nagai et al, Journal of Medicinal Chemistry, American Chemical Society, vol. 22, No. 6, 1979, pp. 677–683.

* cited by examiner

Primary Examiner—Evelyn Mei Huang
(74) Attorney, Agent, or Firm—Mary J. Hosley

(57) ABSTRACT

The present invention provides 2,3,4,4$a$,5,9$b$-hexahydro-1H-pyrido[4,3-b]indoles and 2,3,4,5-tetrahydro-1H-pyrido[4,3-b]indoles. These compounds are 5-HT ligands that are useful for treating diseases wherein modulation of 5-HT activity is desired.

38 Claims, No Drawings

THERAPEUTIC 1H-PYRIDO [4,3-B] INDOLES

CROSS REFERENCE TO RELATED APPLICATIONS

This application claims the benefit of U.S. provisional application Ser. No. 60/310,890 filed on 8 Aug. 2001, under 35 USC 119(e)(i), which is incorporated herein by reference in its entirety.

FIELD OF THE INVENTION

The present invention provides 2,3,4,4a,5,9b-hexahydro-1H-pyrido[4,3-b]indoles and 2,3,4,5-tetrahydro-1H-pyrido[4,3-b]indoles. More specifically, the invention provides compounds of formula (I) described hereinbelow. These compounds are 5-HT ligands, and are useful for treating diseases wherein modulation of 5-HT activity is desired.

BACKGROUND OF THE INVENTION

Serotonin has been implicated in a number of diseases and conditions which originate in the central nervous system. These include diseases and conditions related to sleeping, eating, perceiving pain, controlling body temperature, controlling blood pressure, depression, anxiety, schizophrenia, and other bodily states. R. W. Fuller, Biology of Serotonergic Transmission, 221 (1982); D. J. Boullin, Serotonin in Mental Abnormalities 1:316 (1978); J. Barchas, et al., Serotonin and Behavior, (1973). N. M. Barnes; T. Sharp, A review of central 5-HT receptors and their function, Neuropharmacology, 1999, 38, 1083–1152. Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, receptor-specific agonists and antagonists are of interest for the treatment of a wide range of disorders, including anxiety, depression, hypertension, migraine, obesity, compulsive disorders, schizophrenia, autism, neurodegenerative disorders (e.g., Alzheimer's disease, Parkinsonism, and Huntington's chorea), and chemotherapy-induced vomiting. M. D. Gershon, et al., The Peripheral Actions of 5-Hydroxytryptamine, 246 (1989); P. R. Saxena, et al., Journal of Cardiovascular Pharmacology, 15: Supplement 7 (1990).

The major classes of serotonin receptors (5-$HT_{1-7}$) contain fourteen to eighteen separate receptors that have been formally classified. See Glennon, et al., Neuroscience and Behavioral Reviews, 1990, 14, 35; and D. Hoyer, et al., Pharmacol. Rev. 1994, 46, 157–203. Recently discovered information regarding subtype identity, distribution, structure, and function suggests that it is possible to identify novel, subtype specific agents, having improved therapeutic profiles (e.g., fewer side effects).

For example, the 5-$HT_2$ family of receptors is comprised of 5-$HT_{2A}$, 5-$HT_{2B}$, and 5-$HT_{2C}$ subtypes, which have been grouped together on the basis of primary structure, secondary messenger system, and operational profile. All three subtypes are G-protein coupled, activate phospholipase C as a principal transduction mechanism, and contain a seven-transmembrane domain structure. There are distinct differences in the distribution of the three 5-$HT_2$ subtypes. The 5-$HT_{2B}$ and 5-$HT_{2A}$ receptors are widely distributed in the periphery, while the 5-$HT_{2C}$ receptor has been found only in the central nervous system, being highly expressed in many regions of the human brain. See G. Baxter, et al., Trends in Pharmacol. Sci. 1995, 16, 105–110.

Subtype 5-$HT_{2A}$ has been associated with effects including vasoconstriction, platelet aggregation, and bronchoconstriction, while subtype 5-$HT_{2C}$ has been associated with diseases that include depression, anxiety, obsessive compulsive disorder, panic disorders, phobias, psychiatric syndromes, and obesity. Very little is known about the pharmacologic role of the 5-$HT_{2B}$ receptor. See F. Jenck, et al., Exp. Opin. Invest. Drugs, 1998, 7, 1587–1599; M. Bos, et al., J. Med. Chem., 1997, 40, 2762–2769; J. R. Martin, et al., The Journal of Pharmacology and Experimental Therapeutics, 1998, 286, 913–924; S. M. Bromidge, et al., J. Med. Chem., 1998, 41 1598–1612; G. A. Kennett, IDrugs, 1998, 1, 456–470; and A. Dekeyne, et al., Neuropharmacology, 1999, 38, 415–423.

Japanese Patent Application 63-163347 discusses a vast genus of compounds that are reported to be useful to prevent light fading of organic coloring substances.

A. J. Elliott and H. Guzik, Tetrahedron Letters, 1982, 23, 19, 1983–1984 reports the borane reduction of certain specific indoles.

There is currently a need for pharmaceutical agents that are useful to treat diseases and conditions that are associated with 5-HT receptors.

SUMMARY OF THE INVENTION

In accordance with the present invention, novel compounds which demonstrate useful biological activity, and particularly activity as 5-HT receptor ligands, are provided. Thus, the present invention provides a compound of formula (I):

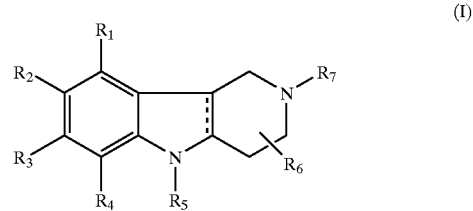

wherein:

$R_1$, $R_2$, $R_3$, and $R_4$ are independently hydrogen, halo, —$CF_3$, —$OCF_3$, —CN, —$NO_2$, $C_{1-8}$alkyl, $C_{2-8}$alkenyl, $C_{2-8}$alkynyl, $C_{3-8}$cycloalkyl, $C_{3-8}$cycloalkenyl, —$OR_8$, —$SR_8$, —C(=O)Ar, Ar, or —$C_{1-8}$alkyleneAr, provided that at least one of $R_1$, $R_2$, $R_3$, or $R_4$ is Ar;

$R_5$ is hydrogen, $C_{1-8}$alkyl, $C_{3-8}$cycloalkyl, aryl, heteroaryl, Het, $R_{10}$C(=O)—, $R_{10}$C(=O)—, $R_{10}SO_2$—, $R_9R_8$NC(=O)—, $R_{10}$C(=S)—, $R_{10}$SC(=O)—, $R_9R_8$NC(=S)—, $R_{10}SO_2$—, $R_9R_8NSO_2$—, $R_{10}S$(=O)—, $R_9R_8$NS(=O)—, $R_dC_{1-8}$alkylene-, or $R_dC_{1-8}$alkyleneC(=O)—;

$R_6$ is hydrogen or $C_{1-4}$alkyl;

$R_7$ is hydrogen, $C_{1-8}$alkyl, $C_{2-8}$alkenyl, $C_{2-8}$alkynyl, halo$C_{1-8}$alkyl, $C_{3-8}$cycloalkyl, $C_{3-8}$cycloalkenyl, $C_{1-8}$alkanoyl, halo$C_{1-8}$alkanoyl, —C(=O)$OR_8$, —C(=O)Ar, Ar, or —$C_{1-8}$alkyleneAr;

each $R_8$ and $R_9$ is independently hydrogen, $C_{1-8}$alkyl, $C_{2-8}$alkenyl, $C_{2-8}$alkynyl, halo$C_{1-8}$alkyl, $C_{3-8}$cycloalkyl, $C_{3-8}$cycloalkenyl, Ar, or —$C_{1-8}$ alkyleneAr; or $R_8$ and $R_9$ together with the nitrogen to which they are attached form a pyrrolidino, piperidino, morpholino, or thiomorpholino ring;

each $R_{10}$ is independently hydrogen, $C_{1-8}$alkyl, $C_{2-8}$alkenyl, $C_{2-8}$alkynyl, halo$C_{1-8}$alkyl, $C_{3-8}$cycloalkyl, $C_{3-8}$cycloalkenyl, Ar, or —$C_{1-8}$alkyleneAr;

the bond represented by - - - is absent or present;

each Ar is independently aryl or heteroaryl;

each $C_{1-8}$alkylene is optionally unsaturated;

each aryl or heteroaryl is optionally substituted with one or more (e.g., 1, 2, 3, or 4) $C_{1-8}$alkyl, $C_{2-8}$alkenyl, $C_{2-8}$alkynyl, $C_{3-8}$cycloalkyl, $C_{3-8}$cycloalkenyl, halo, —CN, —$NO_2$, —$OR_c$, —$CF_3$, —$OCF_3$, —$SR_c$, —$SO_2R_c$, —$SO_2NR_aR_b$, —$NR_aR_b$, —C(=O)$NR_aR_b$, —$NR_cC(=O)R_c$, —$NR_cC(=O)NR_aR_b$, —$CO_2R_c$, or —C(=O)$R_c$;

$R_a$ and $R_b$ are each independently hydrogen, $C_{1-8}$alkyl, $C_{2-8}$alkenyl, $C_{2-8}$alkynyl, $C_{3-8}$cycloalkyl, or $C_{3-8}$cycloalkenyl; or $R_a$ and $R_b$ together with the nitrogen to which they are attached form a pyrrolidino, piperidino, morpholino, or thiomorpholino ring;

each $R_c$ is independently hydrogen, $C_{1-8}$alkyl, $C_{2-8}$alkenyl, $C_{2-8}$alkynyl, $C_{3-8}$cycloalkyl, or $C_{3-8}$cycloalkenyl;

$R_d$ is aryl, Het, heteroaryl, $R_{10}CO_2$—, $R_{10}C(=O)$—, $R_{10}OC(=O)$—, $R_{10}O$—, $R_{10}OC_{1-8}$alkyleneO-, $R_{10}S$—, $R_{10}C(=S)$—, $R_{10}S(=O)$—, $R_{10}SC(=O)$—, $R_{10}C(=O)N(R_{10})$—, $R_{10}C(=S)N(R_{10})$—, $R_9R_8N$—, $R_9R_8NC(=O)$—, $R_9R_8NC(=S)$—, $R_9R_8NS(=O)$—, $R_9R_8NSO_2$—, $R_{10}S(=O)N(R_{10})$—, $R_{10}SO_2N(R_{10})$—;

or a pharmaceutically acceptable salt thereof.

A specific compound of formula (I) is a compound of Formula (II):

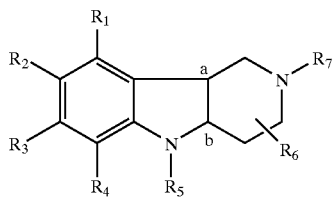

(II)

or a pharmaceutically acceptable salt thereof; wherein $R_1$, $R_2$, $R_3$, $R_4$, $R_5$, $R_6$, and $R_7$ are as defined herein. Specifically, in a compound of Formula (II), the hydrogens at the positions marked a and b can be trans or cis to each other.

Another specific compound of formula (I) is a compound of formula (III):

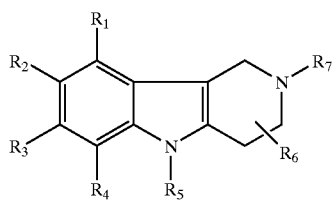

(III)

or a pharmaceutically acceptable salt thereof; wherein $R_1$, $R_2$, $R_3$, $R_4$, $R_5$, $R_6$, and $R_7$ are as defined herein.

In another aspect, the present invention also provides:

a pharmaceutical composition comprising a compound of formula (I), or a pharmaceutically acceptable salt thereof, and a pharmaceutically acceptable excipient (the composition preferably comprises a therapeutically effective amount of the compound or salt), a method for treating a disease or condition in a mammal (e.g., a human) in need thereof, wherein a 5-HT receptor is implicated and modulation of a 5-HT function is desired comprising administering a therapeutically effective amount of a compound of formula (I), or a pharmaceutically acceptable salt thereof to the mammal, a method for treating or preventing a disease or disorder of the central nervous system in a mammal in need thereof comprising administering a therapeutically effective amount of a compound of formula (I), or a pharmaceutically acceptable salt thereof to the mammal, a compound of formula (I) or a pharmaceutically acceptable salt thereof for use in medical diagnosis or therapy (e.g., the treatment or prevention of 5-HT related disease such as anxiety, obesity, depression, or a stress related disease), the use of a compound of formula (I), or a pharmaceutically acceptable salt thereof to prepare a medicament useful for treating or preventing a disease or disorder of the central nervous system in a mammal in need thereof, and a method for modulating 5-HT receptor function, comprising administering an effective modulatory amount of a compound of formula (I), or a pharmaceutically acceptable salt thereof.

The invention also provides novel intermediates and processes disclosed herein that are useful for preparing compounds of formula I.

DETAILED DESCRIPTION OF THE INVENTION

The compounds of the invention are useful for treating or preventing diseases or disorders of the central nervous system. Specific diseases or disorders of the central nervous system for which a compound of formula I may have activity include, but are not limited to: obesity, depression, schizophrenia, schizophreniform disorder, schizoaffective disorder, delusional disorder, a stress related disease (e.g., general anxiety disorder), panic disorder, a phobia, obsessive compulsive disorder, post-traumatic-stress syndrome, immune system depression, a stress induced problem with the urinary, gastrointestinal or cardiovascular system (e.g., stress incontinence), neurodegenerative disorders, autism, chemotherapy-induced vomiting, hypertension, migraine, headaches, cluster headaches, sexual dysfunction in a mammal (e.g., a human) in need thereof, addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a sleep disorder, a specific development disorder, agitation disorder, selective serotonin reuptake inhibition (SSRI) "poop out" syndrome or a Tic disorder (e.g., Tourette's syndrome).

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to.

Aryl denotes a phenyl radical or an ortho-fused bicyclic carbocyclic radical having about nine to ten ring atoms in which at least one ring is aromatic.

Heteroaryl denotes a radical of a monocyclic aromatic ring containing five or six ring atoms consisting of carbon and 1, 2, 3, or 4 heteroatoms each selected from the group consisting of non-peroxide oxygen, sulfur, and N(X) wherein X is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnaolinyl, furazanyl, furyl, imidazolyl, imidizolyl, indazolyl, indolisinyl, indolyl, indolyl, isobenzofuranyl, isoindolyl, isoquinolyl, isothiazolyl, isothiazolyl, isoxazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, xanthenyl, and the like.

The term "Het" generally represents a non aromatic heterocyclic group, which can be saturated or partially unsaturated, containing at least one heteroatom selected from the group consisting of oxygen, nitrogen, and sulfur. Specific, "Het" groups include monocyclic, bicyclic, or tricyclic groups containing one or more heteroatoms selected from the group consisting of oxygen, nitrogen, and sulfur. A "Het" group also can include one or more oxo groups (=O) attached to a ring atom. Nonlimiting examples of Het groups include 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuelidine, thiomorpholine, and the like.

The term "alkylene" refers to a divalent straight or branched hydrocarbon chain (e.g., ethylene —$CH_2CH_2$—). When $C_{1-8}$alkylene is unsaturated, the alkylene chain may comprise one or more (e.g., 1, 2, 3, or 4) double or triple bonds in the chain.

The term "aryl$C_{1-3}$alkylene" for example includes benzyl, phenethyl, naphthylmethyl and the like.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine 5-HT activity using the standard tests which are well known in the art.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g., "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents.

Specifically, $C_{1-8}$alkyl can be methyl, ethyl, propyl, isopropyl, butyl, iso-butyl, sec-butyl, pentyl, 3-pentyl, hexyl, heptyl, or octyl; $C_{2-8}$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $C_{2-8}$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $C_{3-8}$cycloalkyl can be cyclopropyl, cyclobutyl, cyclopentyl, or cyclohexyl; $C_{3-8}$cycloalkyl$C_{1-8}$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $C_{1-8}$alkanoyl can be formyl, acetyl, propanoyl, isopropanoyl, butanoyl, iso-butanoyl, sec-butanoyl, pentanoyl, hexanoyl, or heptanoyl; halo$C_{1-8}$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; halo$C_{1-8}$alkanoyl can be trifluoroacetyl or trichloroacetyl; $C_{1-8}$alkylene can be methylene, 1,2-ethanediyl, 1,3-propanediyl, 1,2-isopropanediyl, 1,4-butanediyl, 1,2-butanediyl, 1,3-iso-butanediyl, 1,2-sec-butanediyl, 1,5-pentanediyl, 1,6-hexanediyl, 1,7-heptanediyl, or 1,8, octanediyl; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_1$ is hydrogen, halo, —$CF_3$, —$OCF_3$, —CN, —$NO_2$, $C_{1-8}$alkyl, $C_{2-8}$alkenyl, $C_{2-8}$alkynyl, $C_{3-8}$cycloalkyl, $C_{3-8}$cycloalkenyl, —$OR_8$, —$SR_8$, Ar, or —$C_{1-8}$alkyleneAr.

Another specific value for $R_1$ is Ar, or —$C_{1-8}$alkyleneAr.

Another specific value for $R_1$ is Ar, wherein Ar is aryl.

Another specific value for $R_1$ is Ar, wherein Ar is heteroaryl.

A more specific value for $R_1$ is 2,4-dichlorophenyl, 2,6-difluorophenyl, 2-fluorophenyl, 2-chlorophenyl, 2-ethoxyphenyl, 2-trifluoromethylphenyl, 2-methylphenyl, 4-methoxy-2-methylphenyl, or 2-chloro-6-fluorophenyl.

A preferred value for $R_1$ is hydrogen, halo, or $C_{1-8}$alkyl.

A specific value for $R_2$ is hydrogen, halo, $-CF_3$, $-OCF_3$, $-CN$, $-NO_2$, $C_{1-8}$alkyl, $C_{2-8}$alkenyl, $C_{2-8}$alkynyl, $C_{3-8}$cycloalkyl, $C_{3-8}$cycloalkenyl, $-OR_8$, $-SR_8$, or Ar, or $-C_{1-8}$alkyleneAr.

Another specific value for $R_2$ is Ar, or $-C_{1-8}$alkyleneAr.

Another specific value for $R_2$ is Ar, wherein Ar is aryl.

Another specific value for $R_2$ is Ar, wherein Ar is heteroaryl.

A more specific value for $R_2$ is 2,4-dichlorophenyl, 2,6-difluorophenyl, 2-fluorophenyl, 2-chlorophenyl, 2-ethoxyphenyl, 2-trifluoromethylphenyl, 2-methylphenyl, 4-methoxy-2-methylphenyl, or 2-chloro-6-fluorophenyl.

A preferred value for $R_2$ is 2,4-dichlorophenyl or 2,6-difluorophenyl.

A specific value for $R_3$ is hydrogen, halo, $-CF_3$, $-OCF_3$, $-CN$, $-NO_2$, $C_{1-8}$alkyl, $C_{2-8}$alkenyl, $C_{2-8}$alkynyl, $C_{3-8}$cycloalkyl, $C_{3-8}$cycloalkenyl, $-OR_8$, $-SR_8$, Ar, or $-C_{1-8}$alkyleneAr.

Another specific value for $R_3$ is Ar, or $-C_{1-8}$alkyleneAr.

Another specific value for $R_3$ is Ar, wherein Ar is aryl.

Another specific value for $R_3$ is Ar, wherein Ar is heteroaryl.

A more specific value for $R_3$ is 2,4-dichlorophenyl, 2,6-difluorophenyl, 2-fluorophenyl, 2-chlorophenyl, 2-ethoxyphenyl, 2-trifluoromethylphenyl, 2-methylphenyl, 4-methoxy-2-methylphenyl, or 2-chloro-6-fluorophenyl.

A preferred value for $R_3$ is hydrogen, halo, or $C_{1-8}$alkyl.

A specific value for $R_4$ is hydrogen, halo, $-CF_3$, $-OCF_3$, $-CN$, $-NO_2$, $C_{1-8}$alkyl, $C_{2-8}$alkenyl, $C_{2-8}$alkynyl, $C_{3-8}$cycloalkyl, $C_{3-8}$cycloalkenyl, $-OR_8$, $-SR_8$, Ar, or $-C_{1-8}$alkyleneAr.

Another specific value for $R_4$ is Ar, or $-C_{1-8}$alkyleneAr.

Another specific value for $R_4$ is Ar, wherein Ar is aryl.

Another specific value for $R_4$ is Ar, wherein Ar is heteroaryl.

A more specific value for $R_4$ is is 2,4-dichlorophenyl, 2,6-difluorophenyl, 2-fluorophenyl, 2-chlorophenyl, 2-ethoxyphenyl, 2-trifluoromethylphenyl, 2-methylphenyl, 4-methoxy-2-methylphenyl, or 2-chloro-6-fluorophenyl.

Another specific value for $R_4$ is hydrogen.

A preferred value for $R_4$ is hydrogen, halo, $-OR_8$, $-SR_8$, or $C_{1-8}$alkyl.

A specific value for $R_5$ is hydrogen, $C_{1-8}$alkyl, or $R_dC_{1-8}$alkylene-.

A specific value for $R_5$ is hydrogen, $R_8R_9NC(=O)C_{1-6}$alkylene-, or aryloxy$C_{1-6}$alkylene-.

Another specific value for $R_5$ is hydrogen.

Another specific value for $R_5$ is hydrogen, $C_{1-8}$alkyl, $R_8R_9NC(=O)CH_2-$, or aryloxy$(CH_2)_2-$.

Another specific value for $R_5$ is hydrogen, $R_8R_9NC(=O)CH_2-$, or aryloxy$(CH_2)_2-$.

Another specific value for $R_5$ is hydrogen, methyl, ethyl, phenyl, benzyl, phenethyl, or benzyloxycarbonyl.

Another specific value for $R_5$ is $C_{1-8}$alkyl, $R_8R_9NC(=O)CH_2-$, $HO(CH_2)_2-$, or aryloxy$(CH_2)_2-$.

Another specific value for $R_5$ is tert-butoxycarbonyl, benzoyl, trifluoroacetyl, or benzyloxycarbonyl.

A preferred value for $R_5$ is hydrogen, $C_{1-8}$alkyl, $R_8R_9NC(=O)CH_2-$, $R_{10}SC_{1-8}$alkylene, or aryloxy$(CH_2)_2-$.

A preferred value for $R_6$ is hydrogen.

A specific value for $R_7$ is hydrogen, $C_{1-8}$alkyl, $C_{2-8}$alkenyl, $C_{2-8}$alkynyl, $C_{3-8}$cycloalkyl, or $C_{3-8}$cycloalkenyl.

A specific value for $R_7$ is tert-butoxycarbonyl, benzoyl, trifluoroacetyl, or benzyloxycarbonyl.

A specific value for $R_7$ is hydrogen or $C_{1-8}$alkyl.

A specific value for $R_7$ is Ar, or $-C_{1-8}$alkyleneAr.

A specific value for $R_7$ is hydrogen, methyl, ethyl, benzyl, or phenethyl.

A preferred value for $R_7$ is hydrogen.

A specific group of compounds are compounds of formula (I) wherein $R_5$, $R_6$, and $R_7$ are hydrogen or a pharmaceutically acceptable salt thereof.

Specifically, the invention also provides a method for treating or preventing anxiety, obesity, depression, schizophrenia, a stress related disease (e.g., general anxiety disorder), panic disorder, a phobia, obsessive compulsive disorder, post-traumatic-stress syndrome, immune system depression, a stress induced problem with the gastrointestinal or cardiovascular system, or sexual dysfunction in a mammal (e.g., a human) in need thereof comprising administering a therapeutically effective amount of a compound of formula I, or a pharmaceutically acceptable salt thereof to the mammal.

Specifically, the invention also provides a method of treating or preventing anxiety, obesity, depression, or a stress related disease, comprising administering to a mammal (e.g., a human) in need thereof, a therapeutically effective amount of a compound of formula (I) or a pharmaceutically acceptable salt thereof.

Specifically, the invention also provides the use of a compound of formula (I) or a pharmaceutically acceptable salt thereof to prepare a medicament for treating or preventing anxiety, obesity, depression, schizophrenia, a stress related disease (e.g., general anxiety disorder), panic disorder, a phobia, obsessive compulsive disorder, post-traumatic-stress syndrome, immune system depression, a stress induced problem with the gastrointestinal or cardiovascular system, or sexual dysfunction in a mammal (e.g., a human) in need thereof.

Specifically, the invention also provides the use of a compound of formula (I) or a pharmaceutically acceptable salt thereof to prepare a medicament for treating or preventing anxiety, obesity, depression, or a stress related disease in a mammal (e.g., a human) in need thereof.

The invention also provides processes useful for preparing compounds of formula (I). Accordingly, the invention provides:

a method for preparing a compound of formula (I), wherein the bond represented by - - - is absent comprising reducing a corresponding compound of formula (I) wherein the bond represented by - - - is present (as illustrated in Scheme 1 below);

a method for preparing a compound of formula (I), wherein $R_5$ is hydrogen, comprising deprotecting a corresponding compound of formula (I) wherein $R_5$ is a suitable nitrogen protecting group;

a method for preparing a compound of formula (I), wherein $R_7$ is hydrogen, comprising deprotecting a corresponding compound of formula (I) wherein $R_7$ is a suitable nitrogen protecting group (as illustrated in Scheme 2);

a method for preparing a compound of formula (I), wherein $R_5$ is other than hydrogen, comprising alkylating or acylating a corresponding compound of formula (I) wherein $R_5$ is hydrogen with the requisite alkylating or acylating agent; and a method for preparing a compound of formula (I), wherein $R_7$ is other than hydrogen, comprising alkylating or acylating a corresponding compound of formula (I) wherein $R_7$ is hydrogen with the requisite alkylating or acylating agent.

Suitable nitrogen protecting groups, as well as methods for their preparation and removal are well known in the art, for example, see Greene, T. W.; Wutz, P. G. M. "Protecting Groups In Organic Synthesis" third edition, 1999, New York, John Wiley & sons, Inc. Preferred protecting groups include benzyloxycarbonyl (CBZ) and benzoyl.

The invention also provides novel intermediates disclosed herein that are useful for preparing compounds of formula (I). For example, the invention provides an intermediate compound of formula (I), wherein either one or both of $R_5$ and $R_7$ are suitable nitrogen protecting groups (e.g., tert-butoxycarbonyl, benzoyl, trifluoroacetyl, or benzyloxycarbonyl).

The invention also provides intermediate salts that are useful for preparing or purifying compounds of formula (I). Suitable methods for preparing salts are known in the art and are disclosed herein. As will be apparent to one skilled in the art, such salts can be converted to the corresponding freebase or to another salt using known methods.

Compounds of the invention can generally be prepared using the synthetic methods illustrated in Schemes 1–8. Starting materials can be prepared by procedures described in these schemes or by procedures that would be well known to one of ordinary skill in organic chemistry. The variables used in the Schemes are as defined herein or as in the claims.

The compounds of this invention can be prepared in a number of ways well known to one skilled in the art of organic synthesis. The compounds of this invention can be prepared as outlined in Schemes 1–8, together with synthetic methods known in the art or variations thereof as appreciated by those skilled in the art.

Scheme 1 illustrates the preparation of compounds wherein only a single substituent of the core heterocycle is non-hydrogen and $R_5$, $R_6$, and $R_7$ are all hydrogen.

Scheme 1

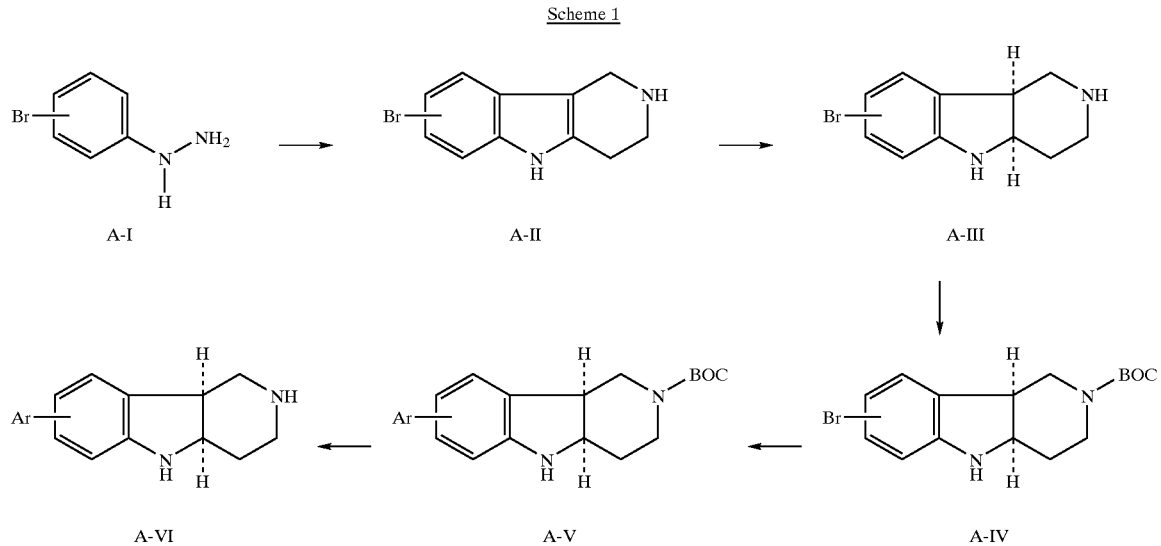

Commercially available bromophenyl hydrazine regioisomers A-I (2-bromo, 3-bromo, and 4-bromo) can be reacted with 4-piperidone under Fisher Indole Synthesis conditions as described, for example, in "*Indoles, Best Synthetic Methods*" (Academic Press, 1999, San Diego, Calif.) to afford the bromoindoles A-II (all regioisomers of A-II are accessible from the three bromophenyl hydrazines). Reduction of these indoles using, for example, sodium cyanoborohydride in trifluoroacetic acid, hydrogen in the presence of a metal catalyst, zinc and a mineral acid, or a borane derivative affords the indolines A-III. Protection of A-III with di-tert-butyl dicarbonate under conditions described in "*Protective Groups in Organic Synthesis, $2^{nd}$ Edition*" (Greene and Wuts, 1991, John Wiley and Sons, Inc., New York) gives A-IV. The aryl bromides A-IV are competent partners for transition metal catalyzed coupling reactions with aryl boronic acids to give the adducts A-I (the so-called Suzuki reaction; see Miyaura, N., et al., *Chem. Rev.*, 1995, 2457 and referenced therein). Typically, the Suzuki reaction is carried out using a palladium catalyst (such as Pd(PPh$_3$)$_4$, Pd(PPh$_3$)$_2$ Cl$_2$, Pd(OAc)$_2$, Pd$_2$(dba)$_3$, etc), a suitable ligand (such as PPh$_3$, Pt-Bu$_3$, Pcy$_3$, etc), a base (such as Na$_2$CO$_3$, Cs$_2$CO$_3$, amines, etc) in a solvent such as DMF, toluene, dioxane, or the like. Lastly, removal of the BOC group under standard conditions (see Greene and Wuts above) affords the final products A-II.

Scheme 2 illustrates the incorporation of R$_5$ and R$_7$ substituents of the intermediate A-I (B-I).

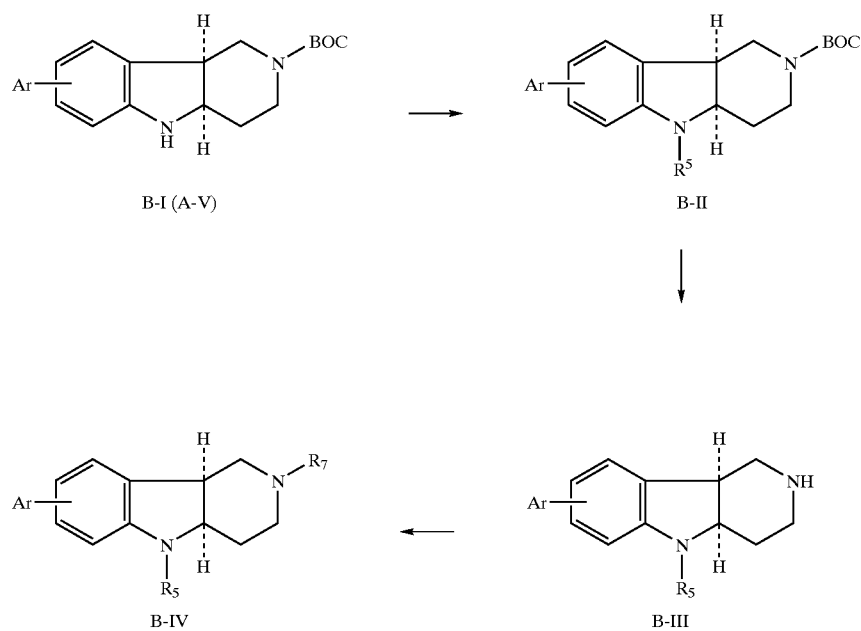

Standard nitrogen alkylation conditions such as treatment of B-I with an alkyl halide or alkyl mesylate in the presence of base such as triethylamine or sodium carbonate in solvents such as acetonitrile or DMF (or see Glennon, et. al., *Med. Chem. Res.*, 1996, 197) or standard reductive alkylation conditions involving treatment with an aldehyde in the presence of sodium cyanoborohydride under acid conditions such as trifluoroacetic acid (see for example Lane, C. F., "Sodium Cyanoborohydride—A Highly Selective Reducing Agent for Organic Functional Groups", *Synthesis*, 1975, 135) gives the R$_5$-substituted products B-II. Removal of the BOC group under standard conditions (trifluoroacetic acid, dichloromethane) gives the secondary amine B-III, which can be derivatized using standard alkylation or reductive amination conditions described above to provide the final products B-IV. In some instances, incorporation of R$_7$ can be accomplished through a standard, two-step sequence involving initial amide formation followed by reduction (LAH or BH$_3$). Scheme 3 illustrates how one skilled in the art can access both cis and trans indolines C-IIc and C-IIt from the common intermediate indole C-I.

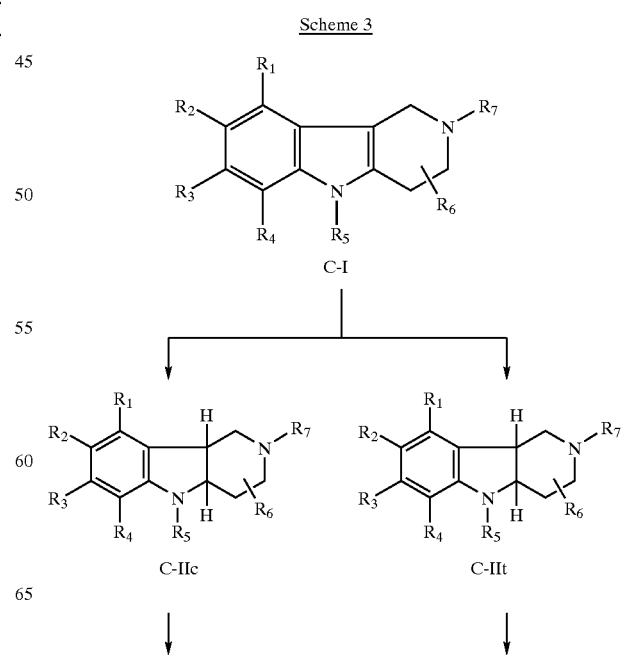

-continued

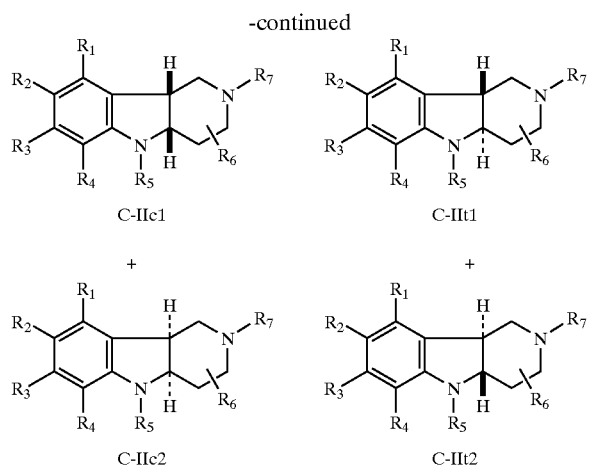

Reduction of C-I (R=H) under conditions such as sodium cyanoborohydride (or sodium triacetoxyborohydride) in acidic solvents such as trifluoroacetic acid gives the cis-indolines C-IIc (R₇=H; derivatization to other R₇ substituents possible at this point as shown in Scheme 2). Separation of the cis-enantiomers is carried out through resolution techniques know in the art, such as chromatographic resolution using a chiral stationary phase (normal or reverse phase) or using a traditional fractional crystallization of diastereomeric salts derived using readily-available chiral acids such as (d)-or (l)-tartaric acid or their derivatives (see for example Kinbara, et al., *J. Chem. Soc., Perkin Trans.*, 2, 1996, 2615 and Tomori, et al., *Bull. Chem. Soc. Jpn.*, 1996, 3581). Reduction of C-I under conditions such as treatment with borane-tetrahydrofuran complex followed by water and trifluoroacetic acid (see for example *Tetrahedron Letters*, 1982, 23, 1983–1984) gives the trans-indolines C-IIt. Resolution of the trans enantiomers is carried out as described above for the cis-isomers.

Scheme 4 illustrates the preparation of substituted phenylhydrazines D-III that may be employed in place of A-I (Scheme 1) and carried through an identical reaction sequence to provide compounds with varying R₁, R₂, R₃, and R₄ groups.

Scheme 4

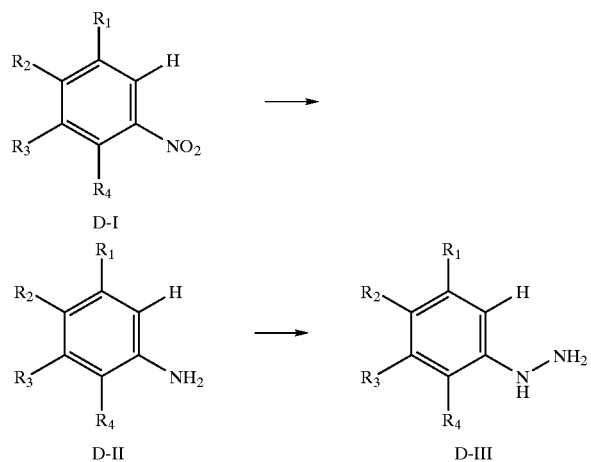

Variations in these groups are accessible through the corresponding nitrobenzenes D-I or anilines D-II, many of which are commercially available or known in the scientific literature, or can be prepared by general procedures known to those skilled in the art (see for example Larock, R. C., "*Comprehensive Organic Transformations*", 1989, VCH Publishers, New York). For example, reduction of the nitro group using a variety of conditions or reagents such as SnCl₂ in acid, LAH, sodium borohydride, hydrazine, or hydrogen in the presence of appropriate catalysts such as palladium, platinum, nickel, etc. (see Hudlicky, M. "*Reductions in Organic Chemistry*", 1984, Ellis Horwood, Ltd., Chichester, UK) gives the corresponding anilines D-II. Conversion of these anilines to the corresponding phenylhydrazines D-III can be accomplished through the well-known nitrosation/reduction sequence (e.g., treatment of D-II with NaNO₂ under acidic conditions, e.g., HOAc, followed by reduction of the resulting N-nitrosoamine with agents such as lithium aluminum hydride or zinc and an organic acid such as acetic or trifluoracetic acid).

Schemes 5 and 6 illustrate an alternative preparation of a subset of compounds of formula I, wherein R₂ is an aryl substituent. Scheme 5 illustrates preparation of the indoline, E-III. Scheme 6 illustrates the conversion of aryl bromides into the corresponding arylboronic acids, F-II and finally to aryl substituted compounds, F-III.

Scheme 5

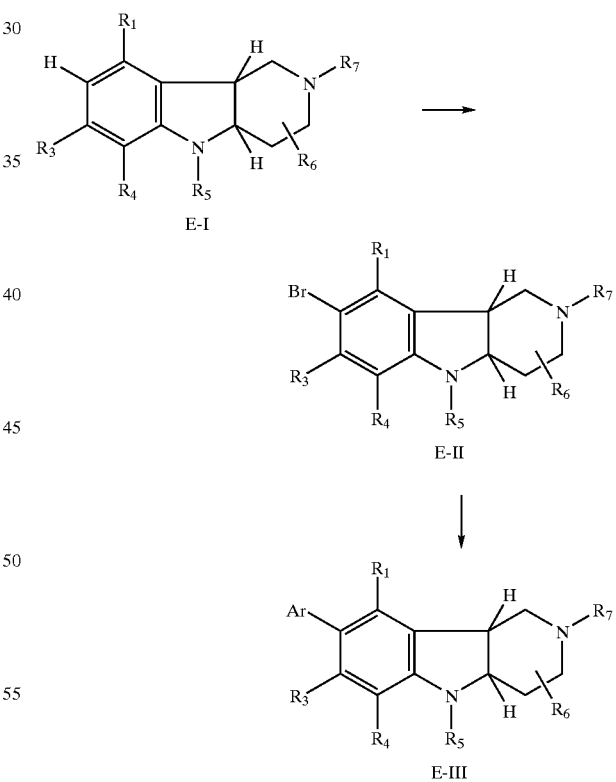

In Scheme 5, the indoline E-I (from a phenylhydrazine prepared as illustrated in Scheme 4 using the procedures of Schemes 1 and 2) can be selectively brominated to provide the arylbromides E-II. Theses aryl bromides are competent partners for transition metal catalyzed coupling reactions with aryl boronic acids to give the adducts E-III.

Scheme 6

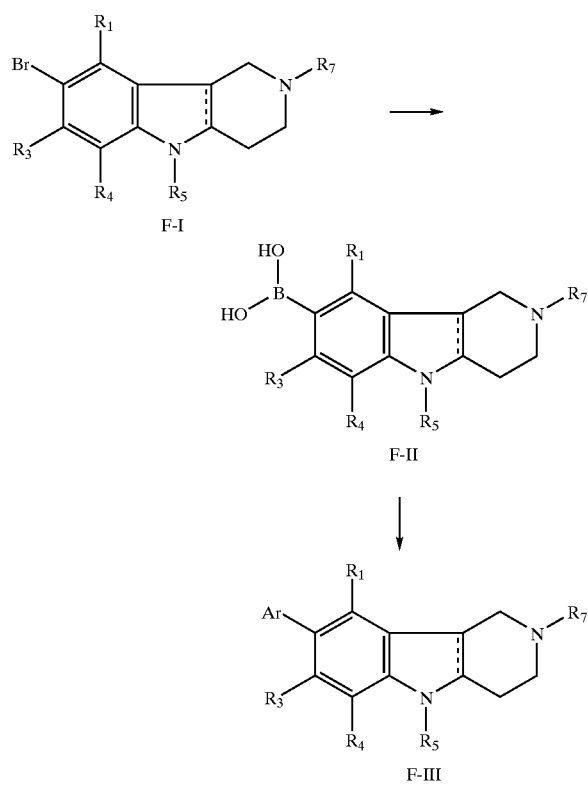

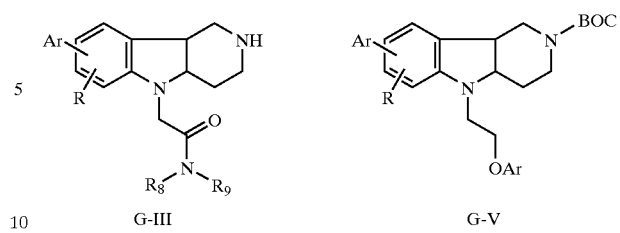

In Scheme 6, the aryl bromides F-I (as either the indole via Scheme 1 or the indoline via Scheme 1 or 5) are converted into the corresponding arylboronic acids F-II using chemistry such as that described by Masuda, et al., *J. Org. Chem*, 2000, 65, 164–168. These arylboronic acids are competent partners in Suzuki couplings with aryl bromides as discussed above for Scheme 1 and 5.

Scheme 7 illustrates the preparation of compounds of formula (I), wherein $R_5$ is an acetamide derivative or an aryloxyethyl derivative.

Alkylation of G-I with ethyl bromoacetate and subsequent hydrolysis provides the carboxylic acid G-II (see for example Glennon, et. al., *Med. Chem. Res.*, 1996, 197). Amide formation via standard coupling protocols (see for example Larock, R. C., "*Comprehensive Organic Transformations*", 1989, VCH Publishers, New York) provides the amides G-III. This approach can be readily adapted to parallel and/or combinatorial chemistry techniques to generate libraries of compounds. In addition, reduction of G-II using agents such as borane in THF gives the alcohol G-IV. Reaction of G-IV with hydroxyaryl compounds under conditions such as those for the Mitsunobu reaction (see for example *Synthesis*, 1981, 1–28) give the aryl ethers G-V. Again, this approach can be readily adapted to parallel and/or combinatorial chemistry techniques to generate libraries of compounds. Chemistry similar to that described in this Scheme could be carried out by one skilled in the art to prepare compound I with other $R_5$ groups.

Scheme 8 illustrates the preparation of compounds of formula (I), wherein $R_6$ is not a hydrogen atom.

Scheme 8

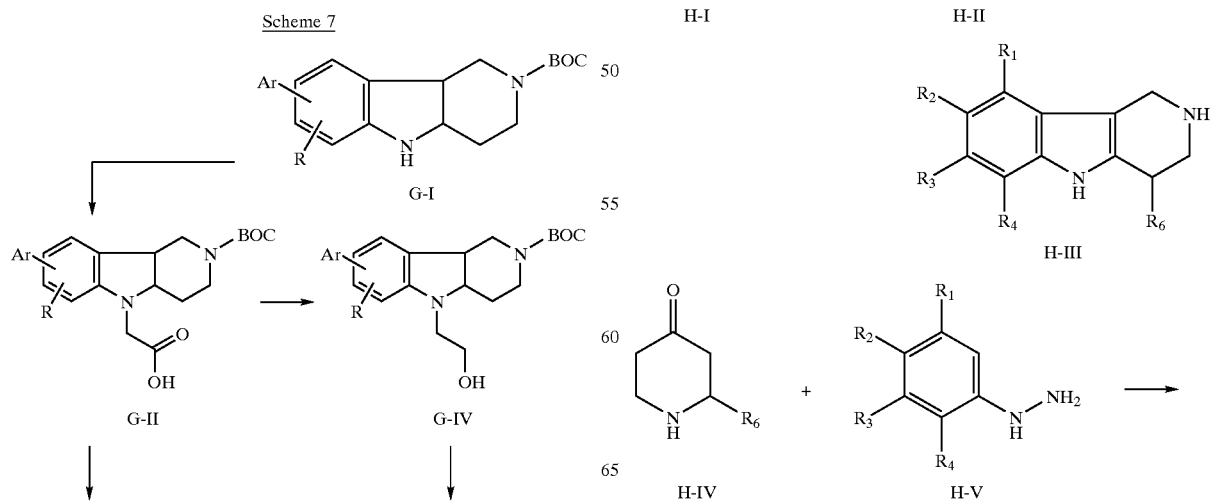

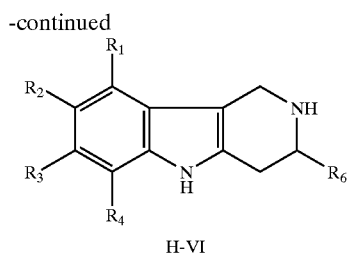

H-VI

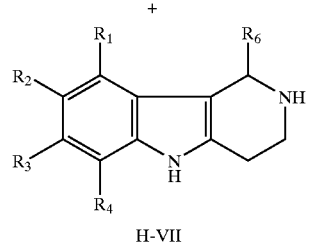

H-VII

These compounds are accessed by reacting 2- or 3-substituted-4-piperidones (H-I and H-IV) with the appropriate phenylhydrazines H-II to give the indoles H-III, H-V, and H-VI. Many of the required 2- or 3-substituted-4-piperidones are known compounds and can be prepared by published procedures. Those that are not known can be prepared by general methods known to those skilled in the art (for example, chiral 2-substituted-4-piperidones can be prepared using the method of Sun, et al., *Tetrahedron Letters*, 2000, 41, 2801–2804).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The ability of a compound of the invention to act as a 5-HT receptor agonist or antagonist can also be determined using in vitro and in vivo assays that are known in the art. The invention provides compounds of formula (I) that act as either agonists or as antagonists of one or more 5-HT receptor subtypes. The compounds of the invention are 5-HT ligands, which typically displace >50% of a radiolabeled test ligand from one or more 5-HT receptor subtype at a concentration of 1 μM. The procedures used for testing such displacement are well known and would be readily available to one skilled in the art. For example, see L. W. Fitzgerald et al., *Mol. Pharmacol*, 2000, 57, 1, 75–81; and D. B. Wainscott, et al., *J. Pharmacol Exp Ther*, 1996, 276, 2, 720–727.

The invention will now be illustrated by the following non-limiting examples.

DESCRIPTION OF PREFERRED EMBODIMENTS

Example 1

8-(2,4-dichlorophenyl)-2,3,4,4a,5,9b-hexahydro-1H-pyrido[4,3-b]indole

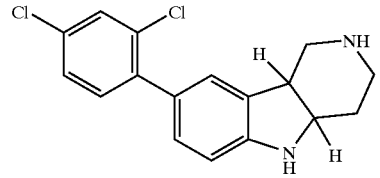

In a 50 ml flask, tert-butyl 8-(2,4-dichlorophenyl)-1,3,4,4a,5,9b-hexahydro-2H-pyrido[4,3-b]indole-2-carboxylate (215 mg) was dissolved in 5 mL dichloromethane and cooled to 0° C. with an ice bath. After the addition of 5 mL trifluoroacetic acid, the reaction stirred at room temperature for 45 minutes. The reaction was concentrated in vacuo then diluted with 5M sodium hydroxide. After three ethyl acetate extractions, the combined organics were washed with brine then dried over magnesium sulfate and concentrated to give crude material which was purified by column chromatography (0.5/5/93.5 ammonium hydroxide/methanol/dichloromethane) to give 101 mg (62%) of the title compound as an off-white solid. MS (ESI+) for $C_{17}H_{16}N_2Cl_2$ m/z 319.1 $(M+H)^+$.

The intermediate tert-butyl 8-(2,4-dichlorophenyl)-1,3,4,4a,5,9b-hexahydro-2H-pyrido[4,3-b]indole-2-carboxylate was prepared as follows.

a. 8-Bromo-2,3,4,4a,5,9b-hexahydro-1H-pyrido[4,3-b]indole. In a 200 mL recovery flask, 8-bromo-2,3,4,5-tetrahydro-1H-pyrido[4,3-b]indole (24 mmol, 6.02 g) was dissolved in 60 mL trifluoroacetic acid and cooled to 0° C. Sodium cyanoborohydride (72 mmol, 4.52 g) was added portionwise over 15 minutes. The reaction stirred at room temperature for 90 minutes, then 60 mL of 6N HCl was added and the reaction was heated to reflux for one hour. After cooling to room temperature, the reaction was made basic with 25% sodium hydroxide. After three chloroform extractions, the combined organics were washed with brine then dried over magnesium sulfate and concentrated to give crude dark orange oil. The crude material was purified by column chromatography (0.5/3.5/96 ammonium hydroxide, methanol, dichloromethane) to give 2.9 g (48%) of 8-bromo-2,3,4,4a,5,9b-hexahydro-1H-pyrido[4,3-b]indole as an off-white foam. HRMS (FAB) calcd for $C_{11}H_{13}BrN_2+H$ 253.0341, found 253.0340.

b. tert-Butyl 8-bromo-1,3,4,4a,5,9b-hexahydro-2H-pyrido[4,3-b]indole-2-carboxylate. In a 250 mL flask equipped with an addition funnel, 8-bromo-2,3,4,4a,5,9b-hexahydro-1H-pyrido[4,3-b]indole (11.1 mmol, 2.82 g) was diluted with 44 mL tetrahydrofuran and 55 mL water. A single portion of potassium carbonate (16.7 mmol, 2.3 g) was added followed by slow addition of a solution of di-t-butyl-dicarbonate (12.2 mmol, 2.66 g) in 11 mL tetrahydrofuran. After 1 hour 45 minutes, the volatiles were removed in vacuo. After three ethyl acetate extractions, the combined organics were washed with brine then dried over magnesium sulfate and concentrated to give crude orange-yellow oil. This crude material was purified by flash chromatography (20% ethyl acetate/heptane) to give 2.7 g (69%) of tert-butyl 8-bromo-1,3,4,4a,5,9b-hexahydro-2H-pyrido[4,3-b]indole-2-carboxylate as an off-white foam. MS (ESI+) for $C_{16}H_{21}N_2BrO_2$ m/z 353.0 (M+H)$^+$.

c. tert-Butyl 8-(2,4-dichlorophenyl)-1,3,4,4a,5,9b-hexahydro-2H-pyrido[4,3-b]indole-2-carboxylate. In a 100 mL flask charged with tert-butyl 8-bromo-1,3,4,4a,5,9b-hexahydro-2H-pyrido[4,3-b]indole-2-carboxylate (1.0 mmol, 0.35g) and 20 mL benzene, 2M sodium carbonate (1.7 mL) was added followed by 2,4-dichlorophenyl boronic acid (2.0 mmol, 0.38g). Bis(triphenylphosphine)palladium (II)chloride (0.5 mmol, 0.035 g) was added and the reaction was heated to reflux for 18 hours. The reaction mixture was concentrated in vacuo then diluted with 1M NaOH. After three ethyl acetate extractions, the combined organics were washed with brine then dried over magnesium sulfate and concentrated to give crude material that was purified by column chromatography (15% ethyl acetate/heptane) to give a mixture of starting material and product. This material was resubjected to the above reaction conditions followed by the same work-up. This material was purified by column chromatography (10:10:80 acetone:dichloromethane:heptane) to give 215 mg (51%) of tert-butyl 8-(2,4-dichlorophenyl)-1,3,4,4a,5,9b-hexahydro-2H-pyrido[4,3-b]indole-2-carboxylate as a foam. MS (ESI+) for $C_{22}H_{24}N_2Cl_2O_2$ m/z 418.9 (M+H)$^+$.

Example 2

6-Bromo-8-(2,4-dichlorophenyl)-2,3,4,4a,5,9b-hexahydro-1H-pyrido[4,3-b]indole:

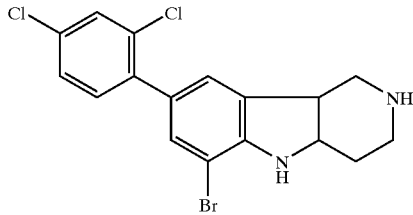

A 200 mL round bottom flask equipped with a reflux condenser was charged with tert-butyl 8-bromo-1,3,4,4a,5,9b-hexahydro-2H-pyrido[4,3-b]indole-2-carboxylate (2.30 g, 6.51 mmol), 2,4-dichloroboronic acid (2.0 g, 10.5 mmol), Pd(PPh$_3$)Cl$_2$ (0.457 g, 0.65 mmol), benzene (65.1 mL) and 2M aq. Na$_2$CO$_3$ (10.74 mL, 21.48 mmol). The reaction was heated to 80° C. for 15 hours, cooled to ambient temperature and partitioned between 1N NaOH and ethyl acetate (2X). The organics were combined, washed with brine, dried over MgSO$_4$, filtered and concentrated to 2.03 grams (74%) of tert-butyl 8-(2,4-dichlorophenyl)-1,3,4,4a,5,9b-hexahydro-2H-pyrido[4,3-b]indole-2-carboxylate as a white foam.

The resulting indole was charged in a 250 mL round bottom flask equipped with a reflux condenser along with di(tert-butyl) dicarbonate (5.2 g, 23.85 mmol), dioxane (48 mL) and diisopropylethylamine (1.66 mL, 9.54 mmol). The mixture was heated to 92° C. for 3.5 hours and cooled to ambient temperature. It was partitioned between 1N NaOH and ethyl acetate (2X). The organics were combined, dried with Na$_2$SO$_4$, filtered and concentrated to give a crude clear oil. The crude oil was purified on a 90 gram silica Biotage column using 20% ethyl acetate as the eluent to give 5.63 g of a mixture of the product mixed with excess di(tert-butyl) dicarbonate. The excess dicarbonate was removed by diluting the mixture into 20 mL of CH$_2$Cl$_2$ followed by the addition of 2M NH$_3$ in MeOH (31.5 mL). After 4 hours of stirring, another 31.5 mL of 2M NH$_3$ in MeOH were added. A precipitate was observed. The reaction was stirred for an additional 1.5 hours, concentrated in vacuo, and partitioned between 1N aq. NaOH and CH$_2$Cl$_2$(2X). The organics were combined, dried with Na$_2$SO$_4$ and concentrated to 3.54 grams of a crude oil. The crude was purified on a 90 gram silica Biotage column using a gradient of 10–20% ethyl acetate in heptane to give 2.03 grams (83%) of di(tert-butyl) 8-(2,4-dichlorophenyl)-3,4,4a,9b-tetrahydro-1H-pyrido[4,3-b]indole-2,5-dicarboxylate. Because of rotational conformers, the 1H NMR was not interpretable. MS (ESI+) for $C_{27}H_{32}Cl_2N_2O_4$ m/z 541.0 (M+Na+H)$^+$.

A dry 25 mL round bottom flask was charged with di(tert-butyl) 8-(2,4-dichlorophenyl)-3,4,4a,9b-tetrahydro-1H-pyrido[4,3-b]indole-2,5-dicarboxylate (0.38 g, 0.74 mmol), DMF (10 mL), N-bromosuccinimide (0.21 g, 1.11 mmol), and stirred at ambient temperature for 18 hours. The reaction was concentrated under high vacuum to remove DMF and partitioned between water and ethyl acetate (2X). The organics were combined, dried with MgSO$_4$, filtered and concentrated to give 461 mg of a crude orange brown oil. Purification of the crude on a 40 gram silica Biotage column using 10% ethyl acetate in heptane gave 217 mg (50%) of di(tert-butyl) 6-bromo-8-(2,4-dichlorophenyl)-3,4,4a,9b-tetrahydro-1H-pyrido[4,3-b]indole-2,5-dicarboxylate as a pale yellow foam.

A 100 mL round bottom flask was charged with a solution of di(tert-butyl) 6-bromo-8-(2,4-dichlorophenyl)-3,4,4a,9b-tetrahydro-1H-pyrido[4,3-b]indole-2,5-dicarboxylate (0.27 g, 0.45 mmol) in CH$_2$Cl$_2$ (5 mL) and cooled to 0° C. with an ice bath. Trifluoroacetic acid (5 mL) was added via pipette, the ice bath was removed, and the mixture was stirred at ambient temperature for 1.5 hours. The reaction was then concentrated in vacuo, and the residue was partitioned between 5 N NaOH and ethyl acetate (2X). The organics were combined, dried with MgSO$_4$, filtered and concentrated to give 280 mg of a crude yellow oil. The crude was purified on a 40 g silica Biotage column using 5% methanol in CH$_2$Cl$_2$ as the eluent to give 151 mg (85%) of 6-bromo-8-(2,4-dichlorophenyl)-2,3,4,4a,5,9b-hexahydro-1H-pyrido[4,3-b]indole as a white foam: $^1$H NMR (300 MHz, CDCl$_3$) δ 7.47 (d, J=2 Hz, 1 H), 7.26 (m, 3 H), 7.10 (s, 1 H), 4.08 (m, 2 H), 3.28 (m, 1 H), 3.14–2.86 (m, 4 H), 1.93–1.80 (m, 3 H); IR (diffuse reflectance) 2937, 2851, 1615, 1572, 1460, 1359, 1314, 1303, 1237, 1102, 1032, 869, 816, 761, 744 cm$^{-1}$. OAMS supporting ions at: ESI+398.8; HRMS (FAB) calcd for $C_{17}H_{15}BRCL_2N_2$ +H$_1$ 396.9874, found 396.9867.

Using procedures similar to those described herein, the following compounds can also be prepared.

(4aS,9bR)-8-Phenyl-2,3,4,4a,5,9b-hexahydro-1H-pyrido[4,3-b]indole

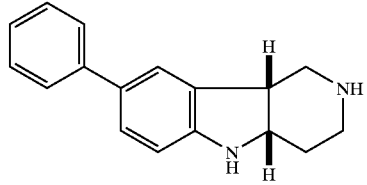

(4aS,9bR)-8-(2,4-Dichlorophenyl)-2,3,4,4a,5,9b-hexahydro-1H-pyrido[4,3-b]indole

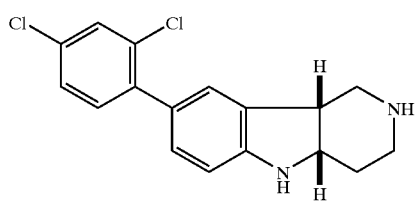

(4aS,9bR)-8-(2,6-Difluorophenyl)-2,3,4,4a,5,9b-hexahydro-1H-pyrido[4,3-b]indole

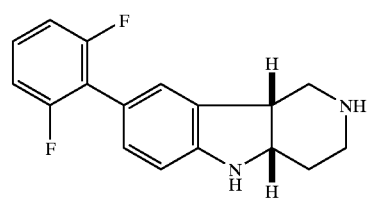

(4aS,9bR)-8-(2-Fluorophenyl)-2,3,4,4a,5,9b-hexahydro-1H-pyrido[4,3-b]indole

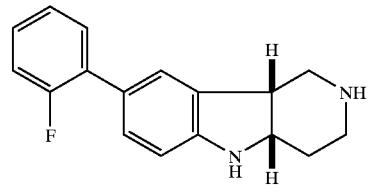

(4aS,9bR)-8-(2-Chlorophenyl)-2,3,4,4a,5,9b-hexahydro-1H-pyrido[4,3-b]indole

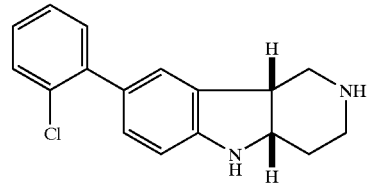

(4aS,9bR)-8-(2-Ethoxyphenyl)-2,3,4,4a,5,9b-hexahydro-1H-pyrido[4,3-b]indole

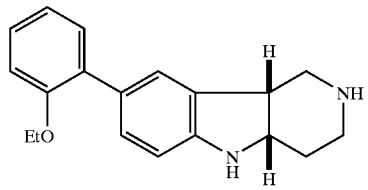

(4aS,9bR)-8-(2-Trifluoromethylphenyl)-2,3,4,4a,5,9b-hexahydro-1H-pyrido[4,3-b]indole

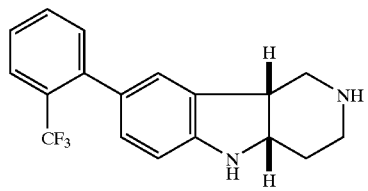

(4aS,9bR)-8-(2-Methylphenyl)-2,3,4,4a,5,9b-hexahydro-1H-pyrido[4,3-b]indole

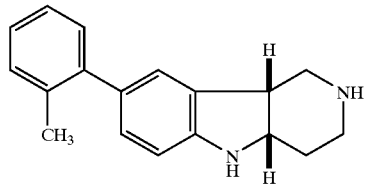

(4aS,9bR)-8-(4-Methoxy-2-methylphenyl)-2,3,4,4a,5,9b-hexahydro-1H-pyrido[4,3-b]indole

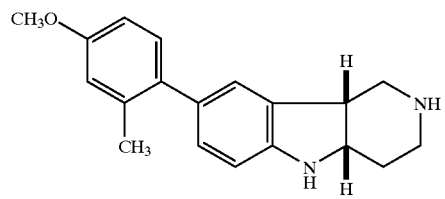

(4aS,9bR)-8-(2-Chloro-6-fluorophenyl)-2,3,4,4a,5,9b-hexahydro-1H-pyrido[4,3-b]indole

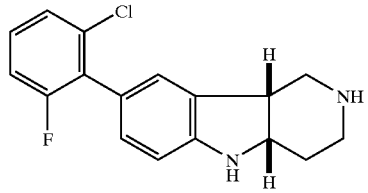

8-(2,4-Dichlorophenyl)-2,3,4,4a,5,9b-hexahydro-1H-pyrido[4,3-b]indole

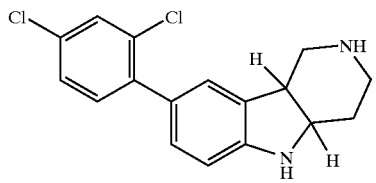

8-(2,4-Dichlorophenyl)-5-methyl-2,3,4,4a,5,9b-hexahydro-1H-pyrido[4,3-b]indole

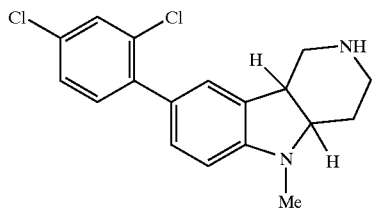

8-(2,4-Dichlorophenyl)-5-ethyl-2,3,4,4a,5,9b-hexahydro-1H-pyrido[4,3-b]indole

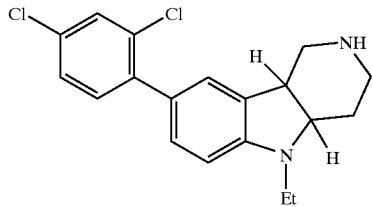

8-(2,4-Dichlorophenyl)-6-(methylthio)-2,3,4,4a,5,9b-hexahydro-1H-pyrido[4,3-b]indole

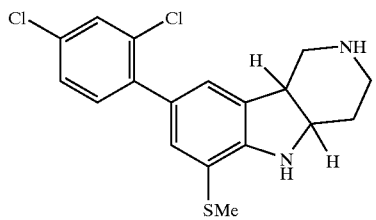

8-(2,4-Dichlorophenyl)-5-methyl-6-(methylthio)-2,3,4,4a,5,9b-hexahydro-1H-pyrido[4,3-b]indole

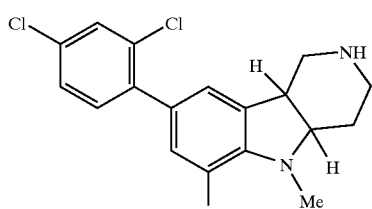

8-(2,4-Dichlorophenyl)-5-ethyl-6-(methylthio)-2,3,4,4a,5,9b-hexahydro-1H-pyrido[4,3-b]indole

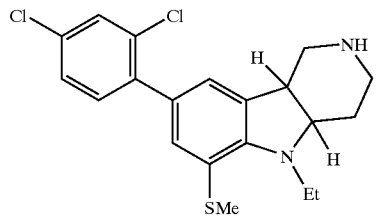

8-(2,4-Dichlorophenyl)-6-(ethylthio)-2,3,4,4a,5,9b-hexahydro-1H-pyrido[4,3-b]indole

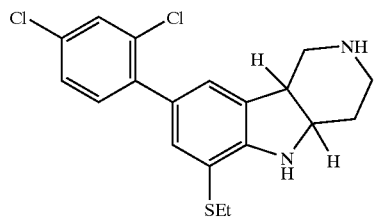

8-(2,4-Dichlorophenyl)-5-methyl-6-(ethylthio)-2,3,4,4a,5,9b-hexahydro-1H-pyrido[4,3-b]indole

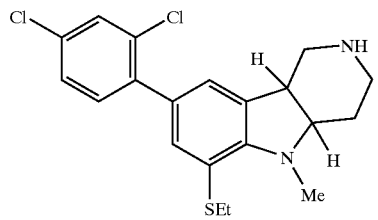

8-(2,4-Dichlorophenyl)-5-ethyl-6-(ethylthio)-2,3,4,4a,5,9b-hexahydro-1H-pyrido[4,3-b]indole

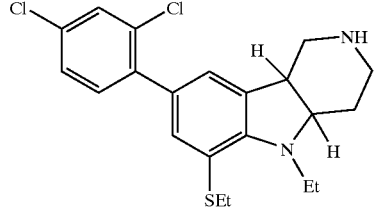

8-(2,4-Dichlorophenyl)-6-methyl-2,3,4,4a,5,9b-hexahydro-1H-pyrido[4,3-b]indole

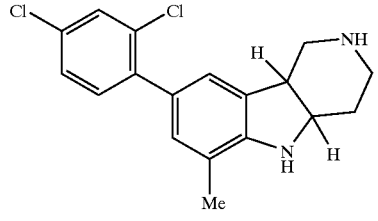

8-(2,4-Dichlorophenyl)-5-methyl-6-methyl-2,3,4,4a, 5,9b-hexahydro-1H-pyrido[4,3-b]indole

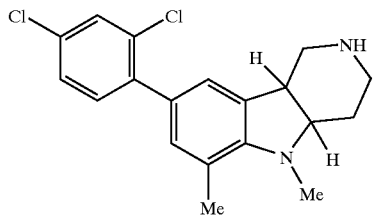

8-(2,4-Dichlorophenyl)-5-ethyl-6-methyl-2,3,4,4a,5,9b-hexahydro-1H-pyrido[4,3-b]indole

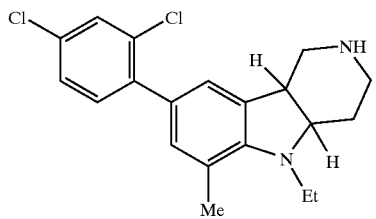

8-(2,4-Dichlorophenyl)-6-ethyl-2,3,4,4a,5,9b-hexahydro-1H-pyrido[4,3-b]indole

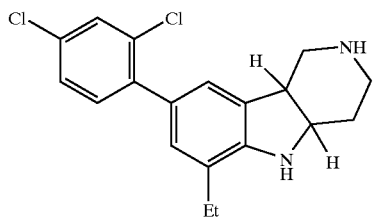

8-(2,4-Dichlorophenyl)-5-methyl-6-ethyl-2,3,4,4a,5,9b-hexahydro-1H-pyrido[4,3-b]indole

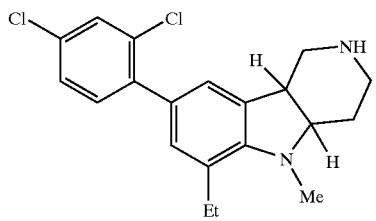

8-(2,4-Dichlorophenyl)-5-ethyl-6-ethyl-2,3,4,4a,5,9b-hexahydro-1H-pyrido[4,3-b]indole

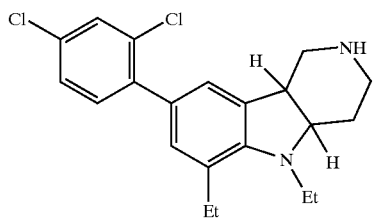

The invention has been described with reference to various specific and preferred embodiments and techniques. However, it should be understood that many variations and modifications may be made while remaining within the spirit and scope of the invention.

What is claimed is:
1. A compound of formula (I):

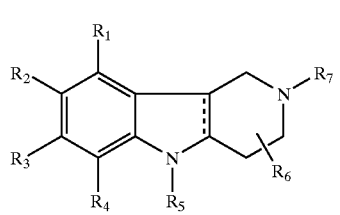

wherein:

$R_1$, $R_2$, $R_3$, and $R_4$ are independently hydrogen, halo, —$CF_3$, —$OCF_3$, —CN, —$NO_2$, $C_{1-8}$alkyl, $C_{2-8}$alkenyl, $C_{2-8}$alkynyl, $C_{3-8}$cycloalkyl, $C_{3-8}$cycloalkenyl, —$OR_8$, —$SR_8$, —C(=O)Ar, Ar, or —$C_{1-8}$alkyleneAr, provided that at least one of $R_1$, $R_2$, $R_3$, or $R_4$ is aryl;

$R_5$ is hydrogen, $C_{1-8}$alkyl, $C_{3-8}$cycloalkyl, aryl, heteroaryl, Het, $R_{10}$C(=O)—, $R_{10}$OC(=O)—, $R_{10}SO_2$—, $R_9R_8$NC(=O)—, $R_{10}$C(=S)—, $R_{10}$SC(=O)—, $R_9R_8$NC(=S)—, $R_{10}SO_2$—, $R_9R_8$NSO$_2$—, $R_{10}$S(=O)—, $R_9R_8$NS(=O)—, $R_dC_{1-8}$alkylene-, or $R_dC_{1-8}$alkyleneC(=O)—;

$R_6$ is hydrogen or $C_{1-4}$alkyl;

$R_7$ is hydrogen, $C_{1-8}$alkyl, $C_{2-8}$alkenyl, $C_{2-8}$alkynyl, halo$C_{1-8}$alkyl, $C_{3-8}$cycloalkyl, $C_{3-8}$cycloalkenyl, $C_{1-8}$alkanoyl, halo$C_{1-8}$alkanoyl, —C(=O)OR$_8$, —C(=O)Ar, Ar, or —$C_{1-8}$alkylenearyl;

each $R_8$ and $R_9$ is independently hydrogen, $C_{1-8}$alkyl, $C_{2-8}$alkenyl, $C_{2-8}$alkynyl, halo$C_{1-8}$alkyl, $C_{3-8}$cycloalkyl, $C_{3-8}$cycloalkenyl, Ar, or —$C_{1-8}$alkyleneAr; or $R_8$ and $R_9$ together with the nitrogen to which they are attached form a pyrrolidino, piperidino, morpholino, or thiomorpholino ring;

each $R_{10}$ is independently hydrogen, $C_{1-8}$alkyl, $C_{2-8}$alkenyl, $C_{2-8}$alkynyl, halo$C_{1-8}$alkyl, $C_{3-8}$cycloalkyl, $C_{3-8}$cycloalkenyl, Ar, or —$C_{1-8}$alkyleneAr;

the bond represented by - - - is absent or present;

each Ar is independently aryl or heteroaryl;

each $C_{1-8}$alkylene is optionally unsaturated;

each aryl or heteroaryl is optionally substituted with one or more $C_{1-8}$alkyl, $C_{2-8}$alkenyl, $C_{2-8}$alkynyl, $C_{3-8}$cycloalkyl, $C_{3-8}$cycloalkenyl, halo, —CN, —$NO_2$, —$OR_c$, —$CF_3$, —$OCF_3$, —$SR_c$, —$SO_2R_c$, —$SO_2NR_aR_b$, —$NR_aR_b$, —C(=O)$NR_aR_b$, —$NR_cC(=O)R_c$, —$NR_cC(=O)NR_aR_b$, —$CO_2R_c$, or —C(=O) $R_c$;

$R_a$ and $R_b$ are each independently hydrogen, $C_{1-8}$alkyl, $C_{2-8}$alkenyl, $C_{2-8}$alkynyl, $C_{3-8}$cycloalkyl, or $C_{3-8}$cycloalkenyl; or $R_a$ and $R_b$ together with the nitrogen to which they are attached form a pyrrolidino, piperidino, morpholino, or thiomorpholino ring;

each $R_c$ is independently hydrogen, $C_{1-8}$alkyl, $C_{2-8}$alkenyl, $C_{2-8}$alkynyl, $C_{3-8}$cycloalkyl, or $C_{3-8}$cycloalkenyl;

$R_d$ is aryl, Het, heteroaryl, $R_{10}CO_2$—, $R_{10}C(=O)$—, $R_{10}OC(=O)$—, $R_{10}O$—, $R_{10}OC_{1-8}$alkyleneO—, $R_{10}S$—, $R_{10}C(=S)$—, $R_{10}S(=O)$—, $R_{10}SC(=O)$—, $R_{10}C(=O)N(R_{10})$—, $R_{10}C(=S)N(R_{10})$—, $R_9R_8N$—, $R_9R_8NC(=O)$—, $R_9R_8NC(=S)$—, $R_9R_8NS(=O)$—, $R_9R_8NSO_2$—, $R_{10}S(=O)N(R_{10})$—, $R_{10}SO_2N(R_{10})$—;
or a pharmaceutically acceptable salt thereof.

2. The compound of claim 1, which is a compound of Formula (II):

(II)

or a pharmaceutically acceptable salt thereof.

3. The compound of claim 2, wherein the hydrogens at the positions marked a and b are trans to each other.

4. The compound of claim 2, wherein the hydrogens at the positions marked a and b are cis to each other.

5. The compound of claim 1, which is a compound of Formula (III):

(III)

or a pharmaceutically acceptable salt thereof.

6. The compound of claim 1, wherein $R_1$ is hydrogen, halo, $C_{1-8}$alkyl, $C_{2-8}$alkenyl, $C_{2-8}$alkynyl, $C_{3-8}$cycloalkyl, $C_{3-8}$cycloalkenyl, Ar, or —$C_{1-8}$alkyleneAr.

7. The compound of claim 1, wherein $R_1$ is hydrogen, halo, or $C_{1-8}$alkyl.

8. The compound of claim 1, wherein $R_1$ is hydrogen.

9. The compound of claim 1, wherein $R_1$ is halo, or $C_{1-8}$alkyl.

10. The compound of claim 1, wherein $R_2$ is halo, —$CF_3$, —$OCF_3$, —CN, —$NO_2$, $C_{1-8}$alkyl, $C_{2-8}$alkenyl, $C_{2-8}$alkynyl, $C_{3-8}$cycloalkyl, $C_{3-8}$cycloalkenyl, —$OR_8$, —$SR_8$, Ar, or —$C_{1-8}$alkyleneAr.

11. The compound of claim 1, wherein $R_2$ is Ar, or —$C_{1-8}$alkyleneAr.

12. The compound of claim 11, wherein Ar is aryl.

13. The compound of claim 11, wherein Ar is heteroaryl.

14. The compound of claim 11, wherein Ar is 2,4-dichlorophenyl, 2,6-difluorophenyl, 2-fluorophenyl, 2-chlorophenyl, 2-ethoxyphenyl, 2-trifluoromethylphenyl, 2-methylphenyl, 4-methoxy-2-methylphenyl, or 2-chloro-6-fluorophenyl.

15. The compound of claim 11, wherein Ar 2,4-dichlorophenyl or 2,6-difluorophenyl.

16. The compound of claim 1, wherein $R_3$ is hydrogen, halo, $C_{1-8}$alkyl, $C_{2-8}$alkenyl, $C_{2-8}$alkynyl, $C_{3-8}$cycloalkyl, $C_{3-8}$cycloalkenyl, Ar, or —$C_{1-8}$alkyleneAr.

17. The compound of claim 1, wherein $R_3$ is hydrogen, halo, or $C_{1-8}$alkyl.

18. The compound of claim 1, wherein $R_3$ is hydrogen.

19. The compound of claim 1, wherein $R_3$ is halo, or $C_{1-8}$alkyl.

20. The compound of claim 1, wherein $R_4$ is hydrogen, halo, $C_{1-8}$alkyl, $C_{2-8}$alkenyl, $C_{2-8}$alkynyl, $C_{3-8}$cycloalkyl, $C_{3-8}$cycloalkenyl, —$OR_8$, —$SR_8$, Ar, or —$C_{1-8}$alkyleneAr.

21. The compound of claim 1, wherein $R_4$ is hydrogen, halo, $C_{1-8}$alkyl, —$OR_8$, —$SR_8$, Ar, or —$C_{1-8}$alkyleneAr.

22. The compound of claim 1, wherein $R_4$ is hydrogen.

23. The compound of claim 1, wherein $R_4$ is halo, $C_{1-8}$alkyl, —$OR_8$, —$SR_8$, Ar, or —$C_{1-8}$alkyleneAr.

24. The compound of claim 23, wherein $R_2$ is Ar, or $C_{1-8}$alkyleneAr.

25. The compound of claim 24, wherein $R_2$ is aryl.

26. The compound of claim 24, wherein $R_2$ is 2,4-dichlorophenyl, 2,6-difluorophenyl, 2-fluorophenyl, 2-chlorophenyl, 2-ethoxyphenyl, 2-trifluoromethylphenyl, 2-methylphenyl, 4-methoxy-2-methylphenyl, or 2-chloro-6-fluorophenyl.

27. The compound of claim 1, wherein $R_5$ is hydrogen, $C_{1-8}$alkyl, or $R_dC_{1-8}$alkylene-.

28. The compound of claim 27, wherein $R_5$ is hydrogen.

29. The compound of claim 27, wherein $R_5$ is $C_{1-8}$alkyl, $R_8R_9NC(=O)CH_2$—, $HO(CH_2)_2$—, or aryloxy$(CH_2)_2$—.

30. The compound of claim 1, wherein $R_5$ is tert-butoxycarbonyl, benzoyl, trifluoroacetyl, or benzyloxycarbonyl.

31. The compound of claim 1, wherein $R_6$ is hydrogen.

32. The compound of claim 1, wherein $R_7$ is hydrogen.

33. The compound of claim 1, wherein $R_7$ is tert-butoxycarbonyl, benzoyl, trifluoroacetyl, or benzyloxycarbonyl.

34. The compound of claim 1 which is (4aS,9bR)-8-phenyl-2,3,4,4a,5,9b-hexahydro-1H-pyrido[4,3-b]indole; (4aS,9bR)-8-(2,4-dichlorophenyl)-2,3,4,4a,5,9b-hexahydro-1H-pyrido[4,3-b]indole; (4aS,9bR)-8-(2,6-difluorophenyl)-2,3,4,4a,5,9b-hexahydro-1H-pyrido [4,3-b]indole; (4aS,9bR)-8-(2-fluorophenyl)-2,3,4,4a,5,9b-hexahydro-1H-pyrido[4,3-b]indole; (4aS,9bR)-8-(2-chlorophenyl)-2,3,4,4a,5,9b-hexahydro-1H-pyrido[4,3-b]indole; (4aS,9bR)-8-(2-ethoxyphenyl)-2,3,4,4a,5,9b-hexahydro-1H-pyrido[4,3-b]indole; (4aS,9bR)-8-(2-trifluoromethylphenyl)-2,3,4,4a,5,9b-hexahydro-1H-pyrido[4,3-b]indole; (4aS,9bR)-8-(2-methylphenyl)-2,3,4,4a,5,9b-hexahydro-1H-pyrido[4,3-b]indole; (4aS,9bR)-8-(4-methoxy-2-methylphenyl)-2,3,4,4a,5,9b-hexahydro-1H-pyrido[4,3-b]indole; or (4aS,9bR)-8-(2-chloro-6-fluorophenyl)-2,3,4,4a,5,9b-hexahydro-1H-pyrido [4,3-b]indole; or a pharmaceutically acceptable salt thereof.

35. The compound of claim 1 which is 8-(2,4-dichlorophenyl)-2,3,4,4a,5,9b-hexahydro-1H-pyrido[4,3-b] indole; 8-(2,4-dichlorophenyl)-5-methyl-2,3,4,4a,5,9b-hexahydro-1H-pyrido[4,3-b]indole; 8-(2,4-dichlorophenyl)-5-ethyl-2,3,4,4a,5,9b-hexahydro-1H-pyrido[4,3-b]indole; 8-(2,4-dichlorophenyl)-6-(methylthio)-2,3,4,4a,5,9b-hexahydro-1H-pyrido[4,3-b]indole; 8-(2,4-dichlorophenyl)-5-methyl-6-(methylthio)-2,3,4,4a,5,9b-hexahydro-1H-pyrido[4,3-b]indole; 8-(2,4-dichlorophenyl)-5-ethyl-6-(methylthio)-2,3,4,4a,5,9b-hexahydro-1H-pyrido[4,3-b] indole; 8-(2,4-dichlorophenyl)-6-(ethylthio)-2,3,4,4a,5,9b-hexahydro-1H-pyrido[4,3-b]indole; 8-(2,4-dichlorophenyl)-5-methyl-6-(ethylthio)-2,3,4,4a,5,9b-hexahydro-1H-pyrido [4,3-b]indole; 8-(2,4-dichlorophenyl)-5-ethyl-6-(ethylthio)-2,3,4,4a,5,9b-hexahydro-1H-pyrido[4,3-b]indole; 8-(2,4-dichlorophenyl)-6-methyl-2,3,4,4a,5,9b-hexahydro-1H-pyrido[4,3-b]indole; 8-(2,4-dichlorophenyl)-5-methyl-6-methyl-2,3,4,4a,5,9b-hexahydro-1H-pyrido[4,3-b]indole; 8-(2,4-dichlorophenyl)-5-ethyl-6-methyl-2,3,4,4a,5,9b-hexahydro-1H-pyrido[4,3-b]indole; 8-(2,4-dichlorophenyl)-6-ethyl-2,3,4,4a,5,9b-hexahydro-1H-pyrido[4,3-b]indole; 8-(2,4-dichlorophenyl)-5-methyl-6-ethyl-2,3,4,4a,5,9b- hexahydro-1H-pyrido[4,3-b]indole; 8-(2,4-dichlorophenyl)-5-ethyl-6-ethyl-2,3,4,4a,5,9b-hexahydro-1H-pyrido[4,3-b]indole; 8-(2,4-dichlorophenyl)-2,3,4,4a,5,9b-hexahydro-1H-pyrido[4,3-b]indole; 6-bromo-8-(2,4-dichlorophenyl)-2,3,4,4a,5,9b-hexahydro-1H-pyrido[4,3]indole; or a pharmaceutically acceptable salt thereof.

36. The compound of claim 35, which is 8-(2,4-dichlorophenyl)-2,3,4,4a,5,9b-hexahydro-1H-pyrido[4,3-b]indole.

37. The compound of claim 35 which is 6-bromo-8-(2,4-dichlorophenyl)-2,3,4,4a,5,9b-hexahydro-1H-pyrido[4,3-b]indole.

38. A pharmaceutical composition comprising a compound of claim 1 and a pharmaceutically acceptable excipient.

* * * * *